United States Patent [19]

Sarantakis

[11] 4,190,575
[45] Feb. 26, 1980

[54] POLYPEPTIDES RELATED TO SOMATOSTATIN

[75] Inventor: Dimitrios Sarantakis, West Chester, Pa.

[73] Assignee: American Home Products Corporation, New York, N.Y.

[21] Appl. No.: 864,173

[22] Filed: Dec. 27, 1977

[51] Int. Cl.² .................... C07C 103/52; A61K 37/00
[52] U.S. Cl. .............................. 260/112.5 S; 424/177
[58] Field of Search .................. 260/112.5 S; 424/177

[56] References Cited

FOREIGN PATENT DOCUMENTS 839405 10/1976 Belgium ............................ 260/112.5 S

OTHER PUBLICATIONS

Rivier et al., J. Med. Chem. 18, 123 (1975).
Rivier et al., Biochem. and Biophys. Res. Commun. 65, 746 (1975).
A. Loffet, Peptides 1976, pp. 427–451.
Meyers et al., Biochem. and Biophys. Res. Commun. 74, 1977, pp. 630–636.

*Primary Examiner*—Delbert R. Phillips

[57] ABSTRACT

Compounds of the formula:

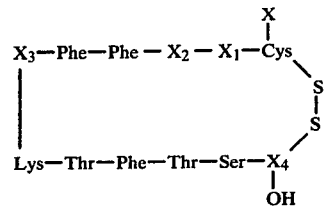

wherein:
X is H, Ala-Gly, Gly-Gly-Gly, Ala-D-Ala, acetyl, or benzoyl;
$X_1$ is Arg or His;
$X_2$ is Glu or Asp;
$X_3$ is Trp or D-Trp; or 6-F-D-Trp; and
$X_4$ is Cys- or D-Cys; or a non-toxic pharmaceutically acceptable acid addition salt thereof; inhibit the secretion of growth hormone and glucagon without materially affecting the secretion of insulin.

5 Claims, No Drawings

POLYPEPTIDES RELATED TO SOMATOSTATIN

Somatostatin is the cyclic disulfide tetradecapeptide of the formula:

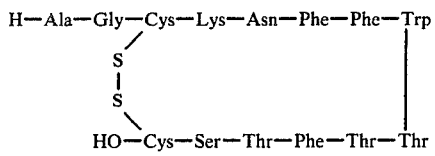

This peptide (I) has been identified as the "somatotropin-release inhibiting factor" (SRIF) which is secreted by the hypothalamus and regulates the secretion of pituitary growth hormone (GH) (somatotropin). [See Brazeau et al., *Science*, 179, 77 (1973), Burgus et al., *Proc. Nat. Acad. Sci.* (USA), 70, 684 (1973), and Ling et al., *Biochemical and Biophysical Res. Communication*, 50, 127 (1973)]. The reduced form of somatostatin (RS) is the linear tetradecapeptide of the formula:

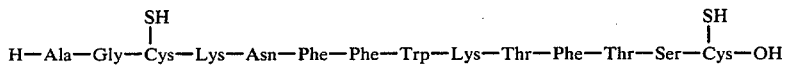

The reduced form (II) has been prepared by total synthesis, [see Rivier et al., C. R. Acad. Sci. Ser. p. Sci. Natur. (Paris), 276, 2737 (1973) and Sarantakis and McKinley, *Biochem. and Biophys. Res. Communications*, 54, 234 (1973)]and it (II) can be converted to somatostatin (I) by oxidation whereby a bridging bond is formed between the two sulfhydryls of the two cysteinyl amino acid residues in the tetradecapeptide.

Various polypeptides which may be regarded as structural modifications of somatostatin have been prepared synthetically and are reported in the chemical literature. Such polypeptides have certain structural features in common with somatostatin and differ from somatostatin in that specific amino acid residues or functional groups originally present in the somatostatin molecule are either missing or are replaced by other amino acid residues or functional groups. The present invention relates to novel synthetic biologically active polypeptides which may be regarded as a structural modification of somatostatin. The polypeptides of the invention differ from somatostatin in the following respects:

(a) the Ala¹-Gly¹ segment is either present, missing, or replaced by Gly-Gly-Gly, Ala-D-Ala, acetyl, or benzoyl;

(b) the Lys⁴ residue is replaced by Arg or His;

(c) the Asn⁵ residue is replaced by Glu or Asp; and (d) the Trp⁸ residue is either present or replaced by D-Trp or 6-F-D-Trp. Modifications of somatostatin missing the Ala¹-Gly² segment and the N-terminal amino group are reported by Rivier et al., *J. Med. Chem.*, 18, 123 (1975). Replacement of the Trp⁸ residue by D-Trp is discussed by Rivier et al., *Biochem. Biophys. Res. Commun.*, 65, 746 (1975). Modifications of somatostatin wherein the Lys⁴-Asn⁵ segment are replaced with other amino acid residues are disclosed in Belgian Patent No. 839,405. Somatostatin derivatives where the Asn⁵ residue is replaced by Asp are described in Belgian Patent No. 827,530.

The invention sought to be patented comprises a chemical compound of Formula III:

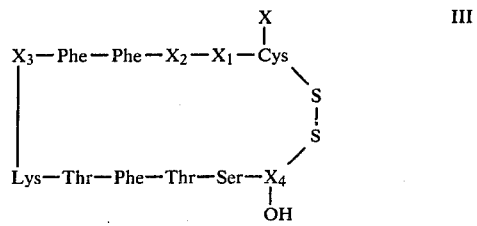

wherein:
X is H, Ala-Gly, Gly-Gly-Gly, Ala-D-Ala, acetyl, or benzoyl;
$X_1$ is Arg or His;
$X_2$ is Glu or Asp;
$X_3$ is Trp or D-Trp; or 6-F-D-Trp; and
$X_4$ is Cys or D-Cys; or

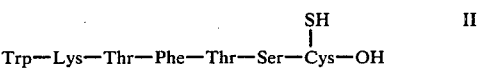

a non-toxic pharmaceutically acceptable acid addition salt thereof.

In addition the invention contemplates the linear form of the compounds of Formula III, i.e. the non-cyclic reduced compounds of Formula IV which contain two free sulfhydryl groups; or a non-toxic pharmaceutically acceptable acid addition salt thereof.

All optically active amino acids and amino acid residues in the polypeptides described herein (Formula II and IV) are in the natural or L-configuration, unless otherwise noted. The symbols identifying the amino acids and the amino acid residues in the polypeptides described herein are those adopted by the IUPACIVB Committee on Biochemical Nomenclature Recommendation (1971), and are described in the *Archives of Biochemistry and Biophysics*, 150, 1-8 (1972). The symbol "6-F-D-Trp" means D-tryptophan in which the 6-position is substituted by fluorine.

The compounds of Formula III and the linear reduced form thereof (Formula IV) inhibit the secretions of growth hormone and glucagon, without materially affecting the secretion of insulin, and, therefore, are useful in controlling serum glucose in the treatment of diabetes. The compounds can be administered either alone or in combination with insulin.

Preferred compounds of Formula III and IV are those wherein:

(a) X is H; $X_1$ is Arg; $X_2$ is Glu; $X_3$ is D-Trp and $X_4$ is Cys; and (b) X is H; $X_1$ is His; $X_2$ is Glu; $X_3$ is D-Trp; and $X_4$ is Cys.

The method of preparation of the above embodiments is described in the Examples. Other embodiments can be prepared using similar methods or obvious modifications thereof. A desired embodiment can be prepared using the exemplified technique by substituting a desired protected amino acid for a particular moiety illustrated.

In general, the polypeptides of this invention are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin and the α-amino protecting group is then removed with trifluoroacetic acid in methylene chloride, trifluoroacetic acid alone or hydrogen chloride in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group, the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid sequence. Diisopropylcarbodiimide is a preferred coupling reagent, although other agents will be apparent to those skilled in the art.

After the desired amino acid sequence has been synthesized, the polypeptide is removed from the resin support by treatment with hydrogen fluoride and anisole to obtain the fully deprotected linear polypeptide. The cyclic disulfide is produced by oxidation of the linear polypeptide, such as by treatment with $K_4Fe(CN)_6$ or by contact with air.

Non-toxic acid addition salts of the linear and cyclic polypeptides are produced by methods well known in the art from organic or inorganic acids which are non-toxic and acceptable for pharmaceutical purposes, such as hydrochloric, hydrobromic, sulfuric, phosphoric, polyphosphoric, maleic, acetic, citric, benzoic, succinic, malonic, or ascorbic acid and the like.

The protecting groups employed throughout the solid phase synthesis are well known to the art. In selecting a particular side chain protecting group to be used in the synthesis of the peptides of this invention, the following rules should be followed: (a) the side chain protecting group must be stable to the reagent and under the reaction conditions selected for removing the α-amino protecting group at each step of the synthesis, (b) the protecting group must retain its protecting properties (i.e., not be split off under coupling conditions), and (c) the side chain protecting group must be removable upon the completion of the synthesis containing the desired amino acid sequence under reaction conditions that will not alter the peptide chain.

Preferred blocking agents are tert-butyloxycarbonyl (BOC), used to protect the α-amino group; benzyl (Bzl), used to protect a side chain hydroxy or carboxyl group; 2-chlorobenzoyloxy (ClZ), used to protect a side chain amino group; tosyl, used to protect a side chain guanidine nitrogen; and p-methoxy benzyl (MBzl), used to protect a side chain mercapto group.

The methods of making and using the compounds of the invention are illustrated in the following Examples:

EXAMPLE 1 tert-Butyloxycarbonyl-S-p-methoxybenzyl-L-cysteinyl-$N^{gn}$-tosyl-L-arginyl-γ-benzyl-L-glutamyl-L-phenylalanyl-L-phenylalanyl-D-tryptophyl-$N^\epsilon$-2-chloro-benzyloxycarbonyl-L-lysyl-O-benzyl-L-threonyl-L-phenylalanyl-O-benzyl-L-threonyl-O-benzyl-L-seryl-S-p-methoxybenzyl-L-cysteine hydroxymethyl-polystyrene ester Chloromethylated polystyrene resin is esterified with Boc-Cys(SMBzl)-OH, according to the procedure of Gisin, Helv. Chim. Acta., 56, 1976 (1973). The amino acid resin ester is then treated according to Schedule A (set forth below), Boc-Ser(Bzl)-OH being employed as the protected amino acid in Step 9 thereof. Schedule A is then repeated in order to incorporate consecutively the following amino acids into the peptido resin:

Boc-Thr(Bzl)-OH
Boc-Phe-OH
Boc-Thr(Bzl)-OH
Boc-Lys(ClZ)-OH
Boc-D-Trp-OH
Boc-Phe-OH
Boc-Phe-OH
Boc-Glu(OBzl)-OH
Boc-Arg(Tos)-OH
Boc-Cys(SMBzl)-OH

Schedule A: (for treatment of the resin ester)

1. Wash with methylene chloride ($CH_2Cl_2$), three times.
2. Treat with trifluoroacetic acid-methylene chloride (1:1, v/v) containing 5% 1,2-ethane dithiol for 5 minutes.
3. Repeat Step 2 for 25 minutes.
4. Wash with $CH_2Cl_2$, three times.
5. Wash with dimethylformamide (DMF).
6. Treat with 12% triethylamine in DMF for 3 minutes.
7. Wash with DMF.
8. Wash with $CH_2Cl_2$, three times.
9. Treat with 4 equivalents of the appropriate protected amino acid in $CH_2Cl_2$-DMF and stir for 5 minutes.
10. Add in two portions over a 30 minute period, 5 equivalents of diisopropylcarbodiimide dissolved in $CH_2Cl_2$. Allow reaction to procede for 6 hours.
11. Wash with DMF, three times.
12. Wash with $CH_2Cl_2$, three times.
13. Test by ninhydrin reaction according to the procedure of Kaiser et al., Annal. Biochem., 34, 595 (1970). In case of incomplete reaction, repeat Steps 9 to 13, as above.

EXAMPLE 2

L-Cysteinyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine cyclic (1–12) disulfide The peptide resin of Example 1 (8.5 g.) was suspended in anisole (16 ml.) and treated with anhydrous liquid hydrogen fluoride (HF) for 45 minutes in an ice-bath, after which time the excess HF was removed under vacuo and the residue extracted with 10% aq. acetic acid. The filtrate was washed with ether and the aqueous layer was poured into 5 liters of water, then the pH was brought to 7 with dilute ammonium hydroxide. The mixture was stirred in the open air for 48 hours then the pH was adjusted to 5 with gl. acetic acid and the peptide absorbed onto Amberlite CG-50 (H+form). The peptidic material was eluted with 50% aq. acetic acid and lyophilized to yield 850 mg. solid material.

The crude product was applied onto a column of Sephadex LH 20 (2.5×150 cm.) and eluted with 10% acetic acid. The fractions 94-130 were pooled and lyophilized to yield 483 mg. of material. This material was applied onto a column of Sephadex G25 (1.5×115 cm.) and eluted with 10% aq. acetic acid. The fractions 43-53 were pooled and lyophilized to give the title peptide, 286 mg.

TLC, avicel precoated glass plates, $R_f$ (BWA, 4:1:1,v/v) 0.40, $R_f$(BWAP, 30:24:6:20, v/v) 0.65.

Amino acid analysis: Thr(2) 1.92, Ser(1) 0.89, Glu(1) 1.03, Cys(2) 1.49, Phe(3) 3, Lys(1) 1.05, Trp(1) 0.81, Arg(1) 1.02.

EXAMPLE 3 tert-Butyloxycarbonyl-S-p-methoxybenzyl-L-cysteinyl-$N^{im}$-tosyl-L-histidyl-$\gamma$-benzyl-L-benzyl-L-glutamyl-L-phenylalanyl-L-phenylalanyl-D-tryptophyl-$N^\epsilon$-2-chlorobenzyloxycarbonyl-L-lysyl-O-benzyl-L-threon-yl-L-phenylalanyl-O-benzyl-L-threonyl-O-benzyl-L-seryl-S-p-methoxy-benzyl-L-cysteine hydroxymethyl-polystyrene ester Chloromethylated polystyrene resin is esterified with Boc-Cys(SMBzl)-OH, according to the procedure of Gisin, Helv. Chim. Acta., 56, 1976 (1973). The amino acid resin is then treated according to Schedule A (see Example 1), Boc-Ser(Bzl)-OH being employed as the protected amino acid in Step 9 thereof. Schedule A is then repeated in order to incorporate consecutively the following amino acids into the peptido resin:

Boc-Thr(Bzl)-OH
Boc-Phe-Oh
Boc-Thr(Bzl)-OH
Boc-Lys(ClZ)-OH
Boc-D-Trp-OH
Boc-Phe-OH
Boc-Phe-OH
Boc-Glu(OBzl)-OH
Boc-His(Tos)-OH
Boc-Cys(SMBzl)-OH

EXAMPLE 4

L-Cysteinyl-L-histidyl-L-glutamyl-L-phenylalanyl-L-phenylalanyl-D-tryptophyl-L-lysyl-L-threonyl-L-phenylalanyl-L-threonyl-L-seryl-L-cysteine cyclic (1-12) disulfide The peptido resin of Example 3 (8 g.) is treated with liquid anhydrous HF as described in Example 2, and the linear disulfhydryl dodecapeptide is cyclized by oxidation with $K_3Fe(CN)_6$ at pH 7.3 and in high dilution. The pH is brought to 5 with gl. acetic acid, and the mixture is treated with BioRad AG3-X4 (Cl form) ion exchange resin, and then absorbed onto Amberlite CG 50 (H+form). The peptidic material is eluted with 30% aq. acetic acid and lyophilized to yield 500 mg. crude material. This material is chromatographed through a column of Sephadex LH 20 to give the title dodecapeptide.

TLC, Avicel precoated glass plates $R_f$(BWA, 4:1:1, v/v) 0.43, $R_f$(tert-AmOH-Py-W, 7:7:6, v/v) 0.74.

Amino acid analysis: Th(2) 1.92, Ser(1) 0.93, Glu(1) 0.94, Cys(2) 1.59, Phe(3) 3, Lys(1) 1.02, His(1) 0.91, Trp(1) 0.81.

EXAMPLE 5

The biological activity of the peptides of Examples 2 and 4 were determined by the following procedure:

Albino male rats are administered Nembutal intraperitoneally at a dose of 50 milligrams per kilogram. Fifteen minutes later a subcutaneous injection of the test compound of physiological saline is administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. An appropriate aliquot is assayed for growth hormone (GH), insulin, and glucagon by radioimmunoassay. The results of the assay are as follows:

| Compound | Dose (ug/kg) | GH ng/kg | Insulin $\mu$U/ml. | Glucagon pg/ml. | No. of Animals |
|---|---|---|---|---|---|
| Control | — | 277 ± 69 | 301 ± 27 | 46 ± 8 | 10 |
| Ex. 2 | 200 | 42 ± 6* | 115 ± 16* | 1.5 ± 1* | 10 |
| Control | — | 216 ± 35 | 283 ± 28 | 55 ± 5 | 10 |
| Ex. 2 | 40 | 28 ± 5* | 158 ± 57 | 12 ± 2* | 10 |
| Control | — | 454 ± 106 | 269 ± 37 | 60 ± 10 | 10 |
| Ex. 4 | 200 | 107 ± 29* | 205 ± 36 | 4 ± 2* | 10 |
| Control | — | 233 ± 35 | 342 ± 45 | 44 ± 4 | 10 |
| Ex. 4 | 50 | 84 ± 17* | 322 ± 40 | 10 ± 4* | 10 |

*p<0.01

The data show that the peptides of Examples 2 and 4, representative of the other peptides of the invention, are effective agents for reducing growth hormone and glucagon without materially affecting insulin levels at a dose of 40 mg/kg and 50 mg/kg, respectively. The peptides of Examples 2 and 4 were also tested for duration of their effect on GH secretion in rats treated with Nembutal. The peptide of Example 1 showed significant inhibition of GH for at least 4 hours at a dose of 1,000 mg/kg (S.C.). The peptide of Example 4 showed no significant inhibition of GH at 2 and 4 hours.

The compounds described herein may be administered to warm-blooded mammals, either intravenously, subcutaneously, intramuscularly, or orally to control serum glucose in the treatment of diabetes. The required dosage will vary with the particular condition being treated, the severity of the condition and the duration of treatment.

The active ingredient may be administered alone or in combination with pharmaceutically acceptable carriers or excipients. Suitable pharmaceutical compositions will be apparent to those skilled in the art.

What is claimed is:

1. A compound of the formula:

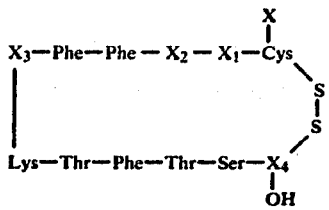

wherein:

X is H, Ala-Gly, Gly-Gly-Gly, Ala-D-Ala, acetyl, or benzoyl;

$X_1$ is Arg or His;

$X_2$ is Glu or Asp;

$X_3$ is Trp or D-Trp; or 6-F-D-Trp; and $X_4$ is Cys or D-Cys; or the reduced linear form thereof, or a non-toxic pharmaceutically acceptable acid addition salt thereof.

2. A compound as defined in claim 1 which is L-cysteinyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine cyclic (1–12) disulfide.

3. A compound as defined in claim 1 which is L-cysteinyl-L-arginyl-L-glutamyl-L-phenylalanyl-L-phenylalanyl-D-tryptophyl-L-lysyl-L-threonyl-L-phenylalanyl-L-threonyl-L-seryl-L-cysteine.

4. A compound as defined in claim 1 which is L-cysteinyl-L-histidyl-L-glutamyl-L-phenylalanyl-L-phenylalanyl-D-tryptophyl-L-lysyl-L-threonyl-L-phenylalanyl-L-threonyl-L-seryl-L-cysteine cyclic (1–12) disulfide.

5. A compound as defined in claim 1 which is L-cysteinyl-L-histidyl-L-glutamyl-L-phenylalanyl-L-phenylalanyl-D-tryptophyl-L-lysyl-L-threonyl-L-phenylalanyl-L-threonyl-L-seryl-L-cysteine.

* * * * *